(12) United States Patent  
Omura et al.

(10) Patent No.: US 7,521,428 B2
(45) Date of Patent: Apr. 21, 2009

(54) MACROLIDE DERIVATIVES HAVING EFFECT OF POTENTIATING ANTIFUNGAL ACTIVITY

(75) Inventors: Satoshi Omura, Tokyo (JP); Hiroshi Tomoda, Chofu (JP); Toshiaki Sunazuka, Funabashi (JP); Masayoshi Arai, Souka (JP); Tohru Nagamitsu, Kawasaki (JP)

(73) Assignee: The Kitasato Institute, Tokyo (JP)

( * ) Notice: Subject to any disclaimer, the term of this patent is extended or adjusted under 35 U.S.C. 154(b) by 974 days.

(21) Appl. No.: 10/472,044

(22) PCT Filed: Oct. 29, 2002

(86) PCT No.: PCT/JP02/11213

§ 371 (c)(1),
(2), (4) Date: May 5, 2004

(87) PCT Pub. No.: WO2004/039823

PCT Pub. Date: May 13, 2004

(65) Prior Publication Data

US 2005/0176655 A1 Aug. 11, 2005

(51) Int. Cl.
*A61K 31/70* (2006.01)
*C07H 17/08* (2006.01)

(52) U.S. Cl. .......................... 514/29; 536/7.2; 536/7.4
(58) Field of Classification Search .................. 536/7.2, 536/7.4
See application file for complete search history.

(56) References Cited

U.S. PATENT DOCUMENTS 4,920,102 A 4/1990 Gidda et al.

FOREIGN PATENT DOCUMENTS

EP 0 296 717 12/1988
WO WO 00/39142 7/2000

OTHER PUBLICATIONS

Management of Invasive Candidal Infections: Results of a Prospective, Randomized, Multicenter Study of Fluconazole Versus Amphotericin B and Review of the Literature, Elias J. Anaissie et al., Clinical Infectious Diseases 1996;23: pp. 964-972,.
"Characterization of an Azole-Resistant *Candida glabrata* Isolate", Hugo Vanden Bossche et al., Dec. 1992, vol. 36, No. 12, pp. 2602-2610.
"Amino Acid Substitutions in the Cytochrome P-450 Lanosterol 14α-Demethylase (CYP51A1) from Azole-Resistant *Candida albicans* Clinical Isolates Contribute to Resistance to Azole Antifungal Agents" Dominique Sanglard et al, vol. 42, No. 2, Feb. 1998, pp. 241-253.

"Analysis of a *Candida albicans* gene that encodes a novel mechanism for resistance to benomyl and methotrexate", Mary E. Fling et al., pp. 318-329.
"Cloning of *Candida albicans* genes conferring resistance to azole antifungal agents: characterization of CDR2, a new multidrug ABC transporter gene", Dominique Sanglard et al. 1997, pp. 405-416.
"PDR16 and PDR17, Two Humologous Genes of *Saccharomyces cerevisiae*, Affect Lipid Biosynthesis and Resistance to Multiple Drugs",. H. Bart van den Hazel et al, vol. 274, No. 4, Issued on Jan. 22, 1999, pp. 1934-1941.
"Motilides, Macrolides with Gastrointestinal Motor Stimulating Activity.[1] I. O-Substituted and Tertiary N-Substituted Derivatives of 8,9-Anhydroerythromycin A 6,9-Hemiacetal" Kazuo Tsuzuki et al. Oct. 1989, pp. 2687-2700, 1989.
"Translactonization in Erythromycins" Isaac O. Kibwage et al., 1987, 52, pp. 990-996.
Structure-Activity Relationship Study of 6-O-Methylerythromycin 9-O-Substituted Oxime Derivates[1] Yutaka Kawashima et al., vol. 42, No. 5, pp. 1088-1095 (1994) Pharmaceutical Society of Japan.
Front page of WO 02/14338, publication date, Feb. 21, 2002, abstract in English.
Patent Abstracts of Japan, 2000-198795, Jul. 18, 2000 (abstract only).

*Primary Examiner*—Elli Peselev
(74) *Attorney, Agent, or Firm*—Young & Thompson

(57) ABSTRACT

Macrolide derivatives having enhancing effect for activities of azole antifungal agents, acting at low concentration and within a short time against fungal infection and reducing the frequency of appearance of resistant microorganisms. One such substance is a compound represented by the formula [I]:

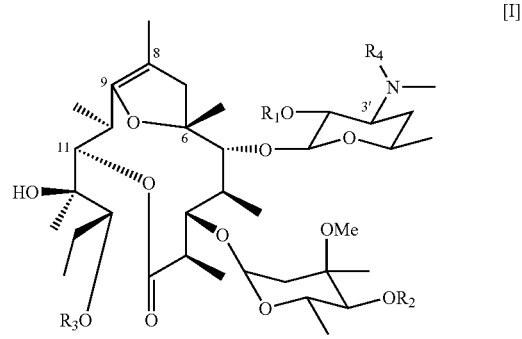

wherein R1 is Ac, R2 and R3 are Ac, and R4 is Me; when R1 is H, R2 and R3 are Ac, and R4 is Me; when R1 is H, R2 and R3 are Ac, and R4 is H, when R1 Bzl, R2 and R3 are Bzl, and R4 is Me; when R1 is Ac, R2 and R3 are Pr, and R4 is Me; when R1 is Ac, R2 and R3 are Hex, and R4 is Me; when R1 is Ac, R2 and R3 are Bzl, and R4 is Me; when R1 is H, R2 and R3 are Pr, and R4 is Me; when R1 is H, R2 and R3 are Hex, and R4 is Me; when R1 is H, R2 and R3 are Bzl, and R4 is Me; when R1 is H, R2 is H, R3 is Bzl, and R4 is Me; when R1 is H, R2 and R3 are Hex, and R4 is H, or when R1 is H, R2 and R3 are Hex, and R4 is Et.

22 Claims, No Drawings

MACROLIDE DERIVATIVES HAVING EFFECT OF POTENTIATING ANTIFUNGAL ACTIVITY

BACKGROUND OF THE INVENTION

The present invention relates to a substance enhancing an effect of antifungal agent used for fungal infection. More particularly, the present invention relates to novel macrolide derivatives having enhancement action for antifungal activity which can enhance antifungal effect in combination with azole antifungal agent used in chemmotherapy for fungal infection accompanied by immunocommpromised condition such as HIV infection and blood disease.

DESCRIPTION OF THE RELATED ART

Examples of known azole compounds used for treatment of fungal infection are 1-[2-(2,4-dichlorobenzyloxy)-2-(2,4-dichlorophenyl)ethyl]imidazole (generic name: miconazole, Sigma Inc., the U.S.), 2,4-difluoro-α, α-bis(1H-1,2,4-triazol-1-yl methyl)benzyl alcohol (generic name: fluconazole, ICN Pharmaceuticals Inc., the U.S.), and (±)-1-sec-butyl-4-[p-[4-[p-[[(2R,4S)-2-(2,4-dichlorophenyl)-2-(1H-1,2,4-triazol-1-yl ethyl)-1,3-dioxolan-4-yl]methoxy]phenyl]-1-piperazinyl] phenyl]-$\Delta^2$-1,2,4-triazolin-5-one (generic name: itraconazole, Kyowa Hakko Co., Japan).

The azole compound is highly safety as compared with polyene antifungal agent used for fungal infection, i.e. 1R, 3S, 5R, 6R, 9R, 11R, 15S, 16R, 17R, 18S, 19E, 21E, 23E, 25E, 27E, 29E, 31E, 33R, 35S, 36S, 37S-33-(3-amino-3,6-dideoxy-β-D-mannopyranosyloxy)-1,3,5,6,9,11,17,37-octahydroxyl-15,16,18-trimethyl-13-oxo-14,39-doxoabicyclo [33.3.1] nonatriaconta-19,21,23,25,27,29,31-heptaene-36-carboxylic acid (generic name: amphotericin B), and is used frequently (Anaissie E. J. et al., Clinical Infectious Diseases, 23, 964-972, 1996).

Recently, problems of appearance of resistant strains caused by long-term or frequent use of azole antifungal agents occur, and development of drugs with low frequency of resistant microbes and high safety is desired. However, development of antifungal agents has been performed mainly for targeting direct fungicidal or fungistatic action, and creating novel agents from standpoint of enforcement of activity of antifungal agent have not been made.

SUMMARY AND OBJECTS OF THE INVENTION

In diseases accompanied with immunocommpromised condition such as HIV infection and blood disease, compromised condition is generated as a result, incidence of fungal infection as opportunistic infection is increased. Many cases of diseases accompanied with immunocommpromised condition are severe and required long-term therapy. For that reason, chemotherapy of fungal infection requires for long term, and drug resistance is easily induced in frequently used azole antifungal agents.

Proposed mechanisms of resistance for azole antifungal agents are: for example, excess expression of P-450 14-α-demethylase, a target enzyme, in *Candida albicans*, and reduced affinity with drugs due to amino acid mutation (Vanden Bossche, H. et al. Antimicrob. Agents and Chemoth., 36, 2602-2610, 1992; Sanglard, D. et al. ibid. 42, 241-253, 1998); reduced intracellular drug concentration by an action of multiple drug excretion transporter such as MSF (major facilitator superfamily) and ABC (ATP binding cassette) (Fling, M. E. et al., Molecular Genetics and Genomics, 227, 318-329, 1991; Sanglard, D. et al., Microbiology, 143, 405-416, 1997).

MDR (multiple drug resistant) genes, PDR 16 and PDR 17, are involved in the lipid metabolism in *Saccharomyces cerevisiae*, and in case of deficient in these genes, microorganisms can be high susceptive against azole compounds (H. Bart van den Hazel et al. J. Biol. Chem., 274, 1934-1941, 1999).

Consequently, drugs which can increase activity of azole antifungal agents can be expected to decrease dosage of drugs and to shorten administration term, as a result, frequency of generation of resistant microorganisms can be decreased. At the same time, combined use of two types of drugs having different skeletal structures or combined use of such drugs for resistant strains against azole compounds are expected to overcome resistance against azole antifungalagents. Consequently, providing drugs having enhanced action for activity of azole antifungal agents is thought to be useful for prevention and therapy of fungal infection and azole resistant fungal infection caused by such as deep sheeted mycosis.

In such conditions, we have studied extensively an action of various macrolide derivatives for enhancing activities of azole antifungal agents, and found the action for enhancing activities of azole antifungal agents in the macrolide derivatives having novel skeletal structure which is different from known azole antifungal agents used for treatment of fungal diseases, and have completed the present invention.

An object of the present invention is to provide novel macrolide derivatives having enhancing effect for activities of antifungal agents, acting at low concentration and within short term against fungal infection and making possibility for reducing frequency of appearence of resistant microorganisms.

The present invention also provides novel macrolide derivatives having enhancing effect for activities of antifungal agents represented by the formula [I]:

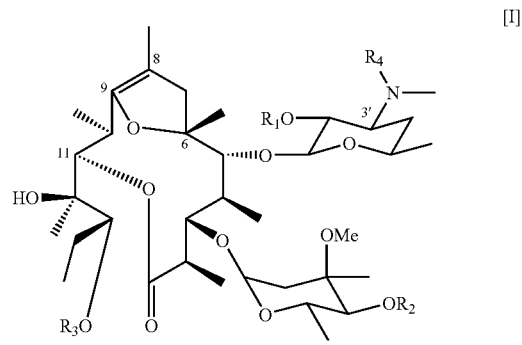

wherein
when R1 is Ac, R2 and R3 are Ac, respectively, and R4 is Me;
when R1 is H, R2 and R3 are Ac, respectively, and R4 is Me;
when R1 is H, R2 and R3 are Ac, respectively, and R4 is H;
when R1 is Bzl, R2 and R3 are Bzl, respectively, and R4 is Me;
when R1 is Ac, R2 and R3 are Pr, respectively, and R4 is Me;
when R1 is Ac, R2 and R3 are Hex, respectively, and R4 is Me;
when R1 is Ac, R2 and R3 are Bzl, respectively, and R4 is Me;
when R1 is H, R2 and R3 are Pr, respectively, and R4 is Me;
when R1 is H, R2 and R3 are Hex, respectively, and R4 is Me;
when R1 is H, R2 and R3 are Bzl, respectively, and R4 is Me;
when R1 is H, R2 is H and R3 are Bzl, and R4 is Me;
when R1 is H, R2 and R3 are Hex, respectively, and R4 is H; or
when R1 is H, R2 and R3 are Hex, respectively, and R4 is Et.

The compound represented by the above formula [I] has an action to enhance activities of azole antifungal agents against Candida albicans and Aspergillus niger, both of which include resistant strains. The present invention provides novel macrolide derivatives having enhancing action of antifungal agent against, for example, Candida albicans such as Candida albicans ATCC 64548 or Candida albicans ATCC 64550, and Aspergillus niger such as Aspergillus niger ATCC 6275.

The present invention also provides novel macrolide derivatives having enhancing effect for activities of antifungal agents represented by the formula [II]:

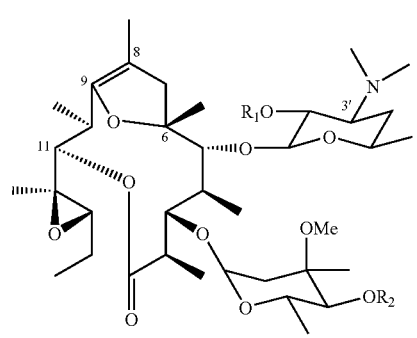

[II]

wherein when R1 is Ac, R2 is SO2Ph; when R1 is Ac, R2 is SO2Bn; or when R1 is H, R2 is SO2Bn.

The compound represented by the above formula [II] has an action to enhance activities of azole antifungal agents against Candida albicans and Aspergillus niger, both of which include resistant strains.

The present invention provides novel macrolide derivatives having enhancing action of antifungal agent against, for example, Candida albicans such as Candida albicans ATCC 64550, and Aspergillus niger such as Aspergillus niger ATCC 6275. The present invention also provides novel macrolide derivatives having enhancing effect for activities of antifungal agents represented by the formula [III]:

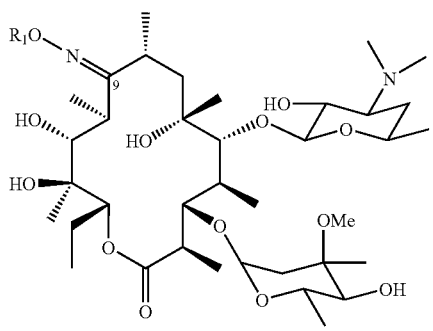

[III]

wherein R1 is —CH2CH=CHCH2—N(piperazine)NH, —CH2CH=CHCH2—NH(CH2CH2)NH2 or —CH2CH2CH=CH2.

The compound represented by the above formula [III] has an action to enhance activities of azole antifungal agents against Candida albicans and Aspergillus niger, both of which include resistant strains. The present invention provides novel macrolide derivatives having enhancing action of antifungal agent against, for example, Candida albicans such as Candida albicans ATCC 6458, and Aspergillus niger such as Aspergillus niger ATCC 6275.

The present invention also provides novel macrolide derivatives having enhancing effect for activities of antifungal agents represented by the formula [IV]:

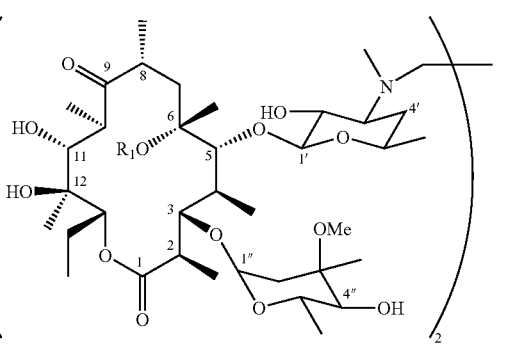

[IV]

wherein R1 is H or Me.

The compound represented by the above formula [IV] has an action to enhance activities of azole antifungal agents against Candida albicans and Aspergillus niger, both of which include resistant strains. The present invention provides novel macrolide derivatives having enhancing action of antifungal agent against, for example, Candida albicans such as Candida albicans ATCC 64548, and Aspergillus niger such as Aspergillus niger ATCC 6275.

The present invention also provides novel macrolide derivatives having enhancing effect for activities of antifungal agents represented by the formula [V]:

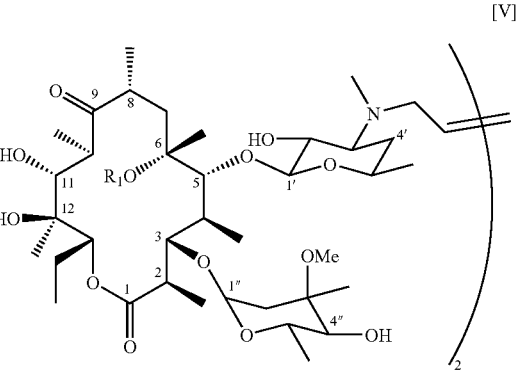

[V]

wherein R1 is H or Me.

The compound represented by the above formula [V] has an action to enhance activities of azole antifungal agents against *Candida albicans* and *Aspergillus niger*, both of which include resistant strains. The present invention provides novel macrolide derivatives having enhancing action of antifungal agent against, for example, *Candida albicans* such as *Candida albicans* ATCC 64548, and *Aspergillus niger* such as *Aspergillus niger* ATCC 6275.

The present invention also provides novel macrolide derivative having enhancing effect for activities of antifungal agents represented by the formula [VI]:

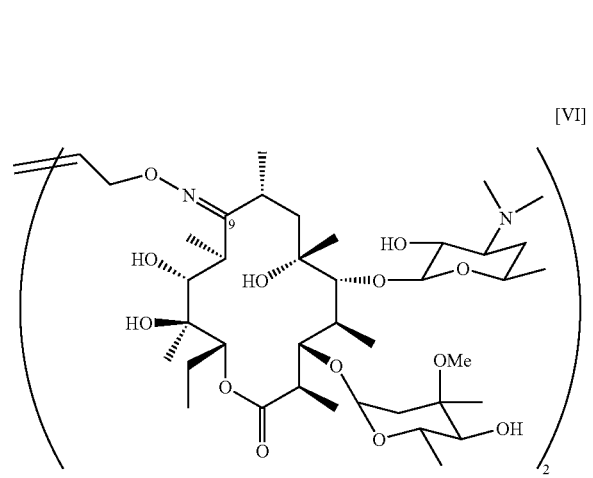

[VI]

The compound represented by the above formula [VI] has an action to enhance activities of azole antifungal agents against *Candida albicans* and *Aspergillus niger* both of which include resistant strains. The present invention provides novel macrolide derivatives having enhancing action of antifungal agents against, for example, *Candida albicans* such as *Candida albicans* ATCC 64548, and *Aspergillus niger* such as *Aspergillus niger* ATCC 6275.

The present invention also provides novel macrolide derivative having enhancing effect for activities of antifungal agents represented by the formula [VII]:

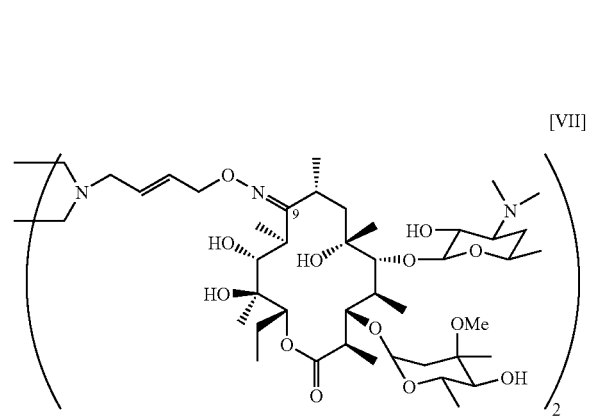

[VII]

The compound represented by the above formula [VII] has an action to enhance activities of azole antifungal agents against *Candida albicans* and *Aspergillus niger*, both of which include resistant strains. The present invention provides novel macrolide derivatives having enhancing action of antifungal agent against, for example, *Candida albicans* such as *Candida albicans* ATCC 64548, and *Aspergillus niger* such as *Aspergillus niger* ATCC 6275.

The present invention also provides novel macrolide derivative having enhancing effect for activities of antifungal agents represented by the formula [VIII]:

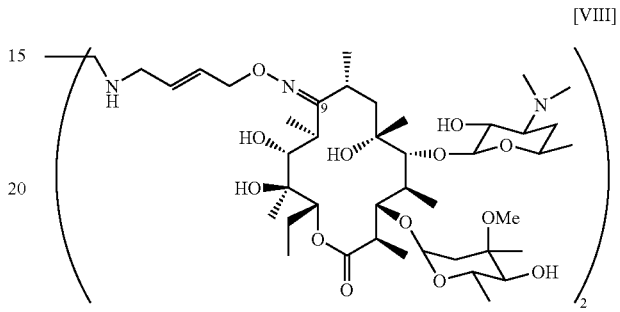

[VIII]

The compound represented by the above formula [VIII] has an action to enhance activities of azole antifungal agents against *Candida albicans*. The present invention provides novel macrolide derivatives having enhancing action of antifungal agents against, for example, *Candida albicans* such as *Candida albicans* ATCC 64548.

The present invention also provides novel macrolide derivative having enhancing effect for activities of antifungal agents represented by the formula [IX]:

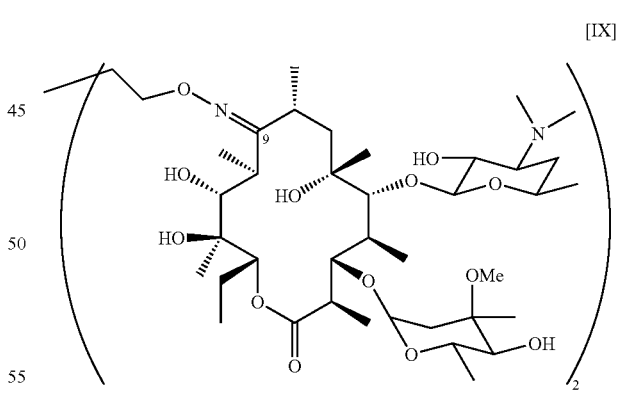

[IX]

The compound represented by the above formula [IX] has an action to enhance activities of azole antifungal agents against *Candida albicans*. The present invention provides novel macrolide derivatives having enhancing action of antifungal agents against, for example, *Candida albicans* such as *Candida albicans* ATCC 64548.

The present invention also provides novel macrolide derivatives having enhancing effect for activities of antifungal agents represented by the formula [X]:

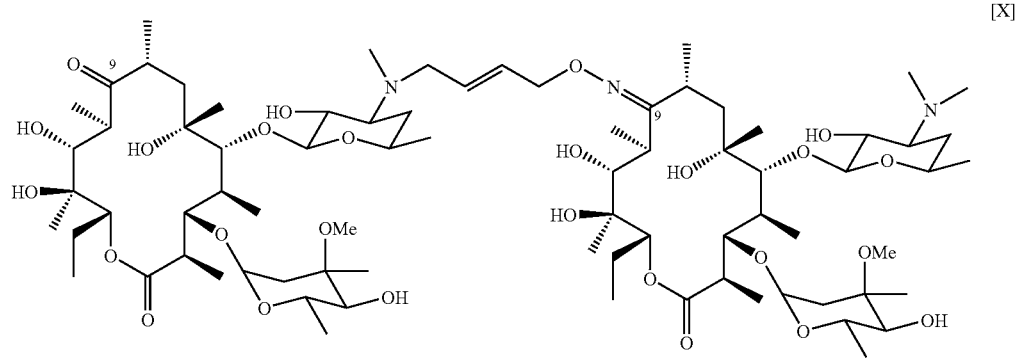

The compound represented by the above formula [X] has an action to enhance activities of azole antifungal agents against *Candida albicans* and *Aspergillus niger*, both of which include resistant strains. The present invention provides novel macrolide derivatives having enhancing action of antifungal agent against, for example, *Candida albicans* such as *Candida albicans* ATCC 64548, and *Aspergillus niger* such as *Aspergillus niger* ATCC 6275.

The present invention also provides novel macrolide derivatives having enhancing effect for activities of antifungal agents represented by the formula [XI]:

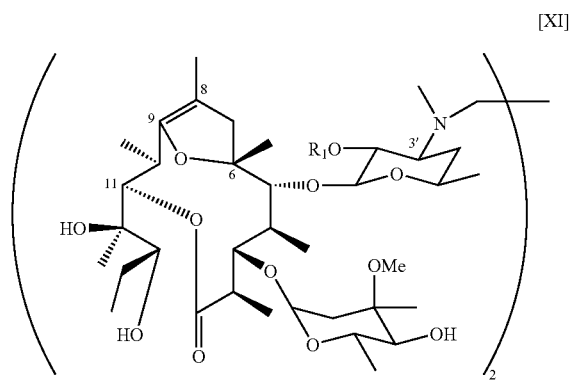

The compound represented by the above formula [XI] has an action to enhance activities of azole antifungal agents against *Candida albicans*. The present invention provides novel macrolide derivatives having enhancing action of antifungal agent against, for example, *Candida albicans* such as *Candida albicans* ATCC 64548.

The present invention provides use of any one of compounds selected from the group consisting of compounds represented by the formula [I] to [XI] for production of pharmaceuticals for enhancing activities of antifungal agents for prevention or treatment of fungal infection accompanied by immunocommpromised condition caused by HIV infection or blood disease. The present invention also provides a substance of any one of compounds selected from the group consisting of compounds represented by the formula [I] to [XI] for production of pharmaceuticals for enhancing activities of antifungal agents for prevention or treatment of fungal infection accompanied by immunocommpromised condition caused by HIV infection or blood diseases.

Compound No. of macrolide derivatives represented by the formula [I] of the present invention, R1, R2, R3 and R4 in the formula, and numbers of examples are listed as follows.

| Compound No. | R1  | R2  | R3  | R4 | Example No. |
|---|---|---|---|---|---|
| EM719 | Ac  | Ac  | Ac  | Me | 1 |
| EM755 | H   | Ac  | Ac  | Me | 2 |
| EM756 | H   | Ac  | Ac  | H  | 3 |
| EM770 | Bzl | Bzl | Bzl | Me | 4 |
| EM771 | Ac  | Pr  | Pr  | Me | 5 |
| EM772 | Ac  | Hex | Hex | Me | 10 |
| EM773 | Ac  | Bzl | Bzl | Me | 6 |
| EM776 | H   | Pr  | Pr  | Me | 7 |
| EM777 | H   | Hex | Hex | Me | 11 |
| EM778 | H   | Bzl | Bzl | Me | 8 |
| EM779 | H   | H   | Bzl | Me | 9 |
| EM852 | H   | Hex | Hex | H  | 12 |
| EM853 | H   | Hex | Hex | Et | 13 |

Compound No. of macrolide derivatives represented by the formula [II] of the present invention, R1 and R2 in the formula, and numbers of examples are listed as follows.

| Compound No. | R1 | R2 | Example No. |
|---|---|---|---|
| EM774 | Ac | SO2Ph | 14 |
| EM775 | Ac | SO2Bn | 15 |
| EM780 | H  | SO2Bn | 16 |

Compound No. of macrolide derivatives represented by the formula [III] of the present invention, R1 in the formula, and numbers of examples are listed as follows.

| Compound No. | R1 | Example No. |
|---|---|---|
| EM762 | —CH$_2$CH=CHCH$_2$—N(piperazine)NH. | 17 |
| EM763 | —CH$_2$CH=CHCH$_2$—NH(piperidine)NH$_2$ | 18 |
| EM769 | —CH$_2$CH$_2$CH=CH$_2$ | 19 |

Compound No. of macrolide derivatives represented by the formula [IV] of the present invention, R1 in the formula, and numbers of examples are listed as follows.

| Compound No. | R1 | Example No. |
|---|---|---|
| EM752 | H | 20 |
| EM753 | Me | 21 |

Compound No. of macrolide derivatives represented by the formula [V] of the present invention, R1 in the formula, and numbers of examples are listed as follows.

| Compound No. | R1 | Example No. |
|---|---|---|
| EM757 | H | 22 |
| EM758 | Me | 23 |

Compound No. of macrolide derivatives represented by the formula [VI] of the present invention, and numbers of examples are listed as follows.

| Compound No. | R1 | Example No. |
|---|---|---|
| EM759 | | 24 |

Compound No. of macrolide derivatives represented by the formula [VII] of the present invention, and numbers of examples are listed as follows.

| Compound No. | Example No. |
|---|---|
| EM760 | 25 |

Compound No. of macrolide derivatives represented by the formula [VIII] of the present invention, and numbers of examples are listed as follows.

| Compound No. | Example No. |
|---|---|
| EM761 | 26 |

Compound No. of macrolide derivatives represented by the formula [IX] of the present invention, and numbers of examples are listed as follows.

| Compound No. | Example No. |
|---|---|
| EM764 | 27 |

Compound No. of macrolide derivatives represented by the formula [X] of the present invention, and numbers of examples are listed as follows.

| Compound No. | Example No. |
|---|---|
| EM765 | 28 |

Compound No. of macrolide derivatives represented by the formula [XI] of the present invention, and numbers of examples are listed as follows.

| Compound No. | Example No. |
|---|---|
| EM741 | 29 |

DETAILED DESCRIPTION OF PREFERRED EMBODIMENT

The present invention is explained in detail by mentioning with examples, but the present invention is not construed as limiting these examples.

REFERENCE EXAMPLE 1

Synthesis of 8,9-Anhydro-pseudoerythromycin A 6,9-hemiketal (EM701)

Synthesis of EM701 was disclosed in detail in WO 02/14338 A1. A glacial acetic acid solution of erythromycin was stirred at room temperature for 2 hours, and aqueous sodium hydrogencarbonate solution was slowly added and neutralized. The reaction mixture was extracted with chloroform. The organic layer was dehydrated by adding anhydrous sodium sulfate, which was removed off by filtration to obtain crude product. The crude product was purified by silica gel column chromatography with chloroform-methanol-aqueous ammonia (10:0.5:0.01→10:1:0.05) to obtain erythromycin A enol ether. Potassium carbonate was added to methanol solution of erythromycin A enol ether and refluxed for 2 hours. After solvent was removed, the residue was dissolved in aqueous sodium hydrogencarbonate and the mixture was extracted with chloroform. The extract was dehydrated with sodium sulfate, filtered and distilled off. The obtained crude product was purified by silica gel column chromatography with chloroform-methanol-aqueous ammonia (10:0.5:0.01→10:1:0.05) to obtain EM701 (white powder).

EXAMPLE 1

Synthesis of 2',4'',13-Tri-O-anhydro-pseudoerythromycin A 6,9-hemiketal (EM719)

Acetic anhydride (327.0 µL) was added to pyridine (2.3 ml) solution of EM701 (165.4 mg, 0.231 mmol) and the mixture was stirred at room temperature for 96 hours. Purified water was added to the mixture and extracted with dichloromethane. The organic layer was washed with saturated brine, dried over anhydrous sodium sulfate, filtered, and removed the solvent to obtain crude product. The crude product was purified by silica gel column chromatography with chloroform-methanol-aqueous ammonia (10:0.5:0.01→10:1:0.05) to give EM719 (118.5 mg, 60%, white powder).

EM719: M.p.: 107-109° C.;
IR (KBr) v: 3467.4, 2973.7, 2935.1, 2879.2, 1700.9, 1637.3, 1457.9, 1380.8, 1265.1, 1166.7, 1126.2, 1079.9, 1037.5, 1016.3 cm$^{-1}$;
HRMS (FAB) m/z: calculated for $C_{35}H_{61}NO_{12}Na$ [M+Na]$^+$ 710.4091, found 710.4060.

EXAMPLE 2

Synthesis of 4",13-Di-O-acetyl-8,9-Anhydro-pseudo erythromycin A 6,9-hemiketal (EM755)

Acetic anhydride (327 μL) was added to pyridine (2.3 ml) solution of EM701 (165.4 mg, 0.231 mmol), and the mixture was stirred at room temperature for 96 hours. Purified water was added to the mixture and extracted with dichloromethane. The organic layer was washed with saturated brine, dried over anhydrouos sodium sulfate, filtered and removed the solvent to obtain crude product. The crude product was purified by silica gel column chromatography with chloroform-methanol-aqueous ammonia (10:0.5:0.01→10:1:0.01) to obtain EM755 (62.6 mg, 34%, white powder)

EM755: M.p.: 108-110° C.;
IR (KBr) v: 3455.8, 2975.6, 2937, 1735.6, 1629.6, 1457.9,. 1378.9, 1243.9, 1168.7, 1078.0, 1043.3, 1016.3 cm$^{-1}$;
HRMS (FAB) m/z: calculated for $C_{41}H_{70}NO_{14}$ [M+H]$^+$ 800.4795, found 800.4784.

EXAMPLE 3

Synthesis of 4",13-Di-O-acetyl-de (3'-N-methyl)-8, 9-Anhydro-pseudoerythromycin A 6,9-hemiketal (EM756)

Sodium acetate (24.5 mg, 0.299 mmol) and iodine (15.2 mg, 0.0598 mmol) were added sequentially to the stirred solution of EM719 (50.3 mg, 0.0598 mmol) in methanol (4.8 mL) and water (1.2 mL) at room temperature. The reaction mixture was stirred at 50° C. for 3 hours. During the reaction, 1N aqueous solution of sodium hydroxide was added dropwise to adjust the pH of the solution to 8.0-9.0. The reaction mixture was diluted with water and extracted with dichloromethane. The extracts were dried over anhydrous sodium sulfate, and concentrated in vacuo, to obtain crude product. The resulting crude product was purified by thin layer chromatography with chloroform-methanol-aqueous ammonia (20:1:0.1) to yield EM756 (49.0 mg, 72%, white powder).

EM756: M.p.: 119-121° C.;
IR (KBr) v: 3450.0, 2975.6, 2939.0, 1735.6, 1457.9, 1376.9, 1241.9, 1126.2, 1093.4, 1041.4, 1016.3 cm$^{-1}$;
HRMS (FAB) m/z: calculated for $C_{40}H_{68}NO_{14}$ [M+H]$^+$ 786.4639, found 786.4649.

EXAMPLE 4

Synthesis of 2',4",13-Tri-O-benzoyl-8,9-Anhydro-pseudoerythromycin A 6,9-hemiketal (EM770)

To the EM701 (33.8 mg, 0.0472 mmol) dissolved in pyridine (1.0 mL) was added dropwise benzoic anhydride (133.6 μL, 0.708 mmol) at room temperature, then DMAP (trace) was added to the solution. The reaction mixture was stirred at room temperature for 5 hours, then at 60° C. for 23 hours. The mixture was poured into water to terminate the reaction and extracted with dichloromethane. The extract was washed with saturated brine, dried over anhydrous sodium sulfate, filtered, and removed the solvent to obtain crude product. The crude product was purified by thin layer chromatography with chloroform-methanol-aqueous ammonia (15:1:0.1) to yield EM770 (27.6 mg, 57%, white powder).

EM770: M.p.: 119-121° C.;
IR (KBr) v: 3374.8, 2975.6, 2937.1, 1724.0, 1672.0, 1602.6, 1452.1, 1378.9, 1338.4, 1268.9, 1170.6, 1097.3, 1070.3, 1016.3, cm$^{-1}$;
HRMS (FAB) m/z: calculated for $C_{58}H_{78}NO_{15}$ [M+H]$^+$ 1028.5371, found 1028.5353.

REFERENCE EXAMPLE 2

Synthesis of 2'-O-acetyl-8,9-Anhydro-pseudoerythro-mycin A 6,9-hemiketal (EM718)

Synthesis of EM718 is described in Kazuo Tsuzuki, Toshiaki Sunazuka, Shogo Marui, Hajime Toyoda, Satoshi Omura, Nobuhiro Inatomi, and Zen Itoh, Chem. Pharm. Bull. 37 (10), 2687-2700, 1989. EM701 (693 mg, 1.0 mmol) was dissolved in acetone (10 ml), added anhydrous aceticacid (918 μl 9.7 mmol), and stirred at room temperature for 40 minutes. The reaction mixture was diluted with water (50 ml) and the mixture was extracted with chloroform (50 ml). Chloroform layer was dehydrated by adding anhydrous sodium sulfate, and remove the solvent to obtain crude product. The crude product was purified by silica gel column chromatography using chloroform-methanol-aqueous ammonia. (10:0.5:0.1) to obtain EM718 (586 mg, 80%, amorphous white solid).

EXAMPLE 5

Synthesis of 2'-O-acetyl-4",13-Di-O-propionyl-8,9-Anhydro-pseudoerythromycin A 6,9-hemiketal (EM771)

To the solution of EM718 (34.0 mg, 0.0449 mmol) in pyridine (1.0 mL) was added dropwise propionic anhydride (86.3 μL, 0.673 mmol) at room temperature, then DMAP (trace) was added to the solution. The reaction mixture was stirred at room temperature for 18 hours. The mixture was poured into water to terminate the reaction and extracted with dichloromethane. The extract was washed with saturated brine, dried over anhydrous sodium sulfate, filtered, and removed the solvent to obtain crude product. The crude product was purified by thin layer chromatography with chloroform-methanol-aqueous ammonia (15:1:0.1) to yield EM771 (27.6 mg, 71%, white powder)

EM771: M.p.: 96-98° C.;
IR (KBr) v: 3521.4, 3446.2, 2977.6, 2940.9, 2883.1, 1745.3, 1463.7, 1375.0, 1344.1, 1240.0, 1170.6, 1066.4, 1016.3 cm$^{-1}$;
HRMS (FAB) m/z: calculated for $C_{45}H_{75}NO_{15}Na$ [M+Na]$^+$ 892.5034, found 892.5037.

EXAMPLE 6

Synthesis of 2'-O-acetyl-4",13-Di-O-benzoyl-8,9-Anhydro-pseudoerythromycin A 6,9-hemiketal (EM773)

To the solution of EM718 (64.0 mg, 0.0845 mmol) in pyridine (1.7 mL) was added dropwise benzoic anhydride, (159.4 μL, 0.845 mmol) at room temperature, then DMAP (trace) was added to the solution. The reaction mixture was stirred at room temperature for 120 hours. The mixture was poured into water to terminate the reaction and extracted with dichloromethane. The extract was washed with saturate brine, dried over anhydrous sodium sulfate, filtered, and distilled of the solvent to obtain crude product. The crude product was purified by thin layer chromatography with chloroform-methanol-aqueous ammonia (15:1:0.1) to yield EM773 (34.1 mg, 42%, white powder) and a by-product (20.6 mg) which was used for preparing EM779.

EM773: M.p.: 108-110° C.;

IR (KBr) ν: 3473.2, 2975.6, 2939.0, 2881.1, 1745.3, 1375.0, 1338.4, 1268.9, 1168.7, 1110.8, 1070.3, 1016.3 cm$^{-1}$;

HRMS (FAB) m/z: calculated- for $C_{53}H_{75}NO_{15}Na$ [M+Na]$^+$ 988.5034, found 988.5030.

EXAMPLE 7

Synthesis of 4",13-Di-O-propionyl-8,9-Anhydro-pseudo-erythromycin A 6,9-hemiketal (EM776)

EM771 (27.6 mg, 00317 mmol) was dissolved in methanol (1.0 mL) and stirred at room temperature for 48 hours. After the removal of methanol in vacuo, the residue was purified by thin layer chromatography with chloroform-methanol-aqueous ammonia (15:1:0.1) to yield EM776 (25.4 mg, 97%, white powder).

EM776: M.p.: 138-140° C.;

IR (KBr): ν: 3430.7, 2977.6, 2933.2, 1739.5, 1621.8, 1589.1, 1456.0, 1419.4, 1384.6, 1344.1, 1315.2, 1243.9, 1164.8, 1124.3, 1074.2, 1016.3 cm$^{-1}$;

HRMS (FAB) m/z: calculated for $C_{43}H_{73}NO_{14}Na$ [M+Na]$^+$ 850.4929, found 850.4928.

EXAMPLE 8

Synthesis of 4",13-Di-O-benzoyl-8,9-Anhydro-pseudo-erythromycin A 6,9-hemiketal (EM778)

EM773 (34.1 mg, 0.0353 mmol) was dissolved in methanol (1.0 mL) and stirred at room temperature for 96 hours. After the removal of methanol in vacuo, the residue was purified by thin layer chromatography with chloroform-methanol-aqueous ammonia (15:1:0.1) to yield EM778 (32.0 mg, 98%, white powder).

EM778: M.p.: 113-116° C.;

IR (KBr) ν: 3486.7, 2977.6, 2939.0, 2879.2, 1724.0, 1602.6, 1585.2, 1452.1, 1382.7, 1334.5, 1268.9, 1170.6, 1112.7, 1070.3, 1018.2 cm$^{-1}$;

HRMS (FAB) m/z: calculated for $C_{51}H_{74}NO_{14}$ [M+H]$^+$ 924.5109, found 924.5120.

EXAMPLE 9

Synthesis of 13-O-benzoyl-8,9-Anhydro-pseudoerythro-mycin A 6,9-hemiketal (EM779)

The by-product mixture (20.6 mg), which had been obtained in the preparation of EM773, was dissolved in methanol (1.0 mL) and stirred at room temperature for 96 hours. After the removal of methanol in vacuo, the residue was purified by thin layer chromatography with chloroform-methanol-aqueous ammonia (15:1:0.1) to yield EM779 (18.6 mg, 90%, white powder).

EM779: M.p.: 125-127° C.;

IR (KBr) ν: 3467.4, 3436.5, 2971.8, 2879.2, 1722.1, 1631.5, 1454.1, 1380.8, 1317.1, 1270.9, 1166.7, 1110.8, 1074.2, 1016.3, 937.2 cm$^{-1}$;

HRMS (FAB) m/z: calculated for $C_{44}H_{70}NO_{13}$ [M+H]$^+$ 820.4847, found 820.4859.

EXAMPLE 10

Synthesis of 2'-O-acetyl-4",13-Di-O-hexanoyl-8,9-Anhydro-pseudoerythromycin A 6,9-hemiketal (EM772)

To the solution of EM718 (36.5 mg, 0.0482 mmol) in pyridine (1.0 mL) was added dropwise hexanoic anhydride (167.3 μL, 0.723 mmol) at room temperature, then DMAP (trace) was added to the solution. The reaction mixture was stirred at room temperature for 18 hours. The mixture was poured into water to terminate the reaction and extracted with dichloromethane. The extract was washed with saturated brine, dried over anhydrous sodium sulfate, filtered, and distilled off the solvent to obtain the crude product. The crude product was purified by thin layer chromatography with chloroform-methanol-aqueous ammonia (15:1:0.1) to yield EM772 (32.5 mg, 71%, white powder).

EM772: M.p.: 90-91° C.;

IR (KBr) ν: 3519.5, 2971.8, 2937.1, 2861.8, 2831.0, 2782.8, 1743.3, 1457.9, 1375.0, 1340.3, 1241.9, 1168.7, 1095.4, 1058.7, 1016.3 cm$^{-1}$;

HRMS (FAB) m/z: calculated for $C_{58}H_{77}NO_{15}Na$ [M+Na]$^+$ 1050.5191, found 1050.5210.

EXAMPLE 11

Synthesis of 4",13-Di-O-hexanoyl-8,9-Anhydro-pseudo-erythromycin A 6,9-hemiketal (EM777)

EM772 (32.5 mg, 0.0341 mmol) was dissolved in methanol (1.0 mL) and stirred at room temperature for 48 hours. After the removal of methanol in vacuo, the residue was purified by thin layer chromatography with chloroform-methanol-aqueous ammonia (15:1:0.1) to yield EM777 (31.1 mg, 99%, white powder).

EM777: M.p.: 94-96° C.;

IR (KBr) ν: 3648.4, 3465.5, 2962.1, 2933.2, 2861.8, 1737.5, 1629.6, 1456.0, 1382.7, 1243.9, 1166.7, 1110.8, 1074.2, 1016.3 cm$^{-1}$;

HRMS (FAB) m/z: calculated for $C_{49}H_{85}NO_{14}Na$ [M+Na]$^+$ 934.5868, found 934.5867.

EXAMPLE 12

Synthesis of 4",13-Di-O-hexanoyl-8,9-Anhydro-pseudo-erythromycin A 6,9-hemiketal (EM852)

EM777 (108.4 mg, 0.119 mmol) was dissolved in 80% methanol (1.0 mL), and sodium acetate (48.8 mg, 0.595 mmol) and iodine (30.2 mg, 0.119 mmol) were gradually added by small portions, then stirred at 47° C. for 75 minutes. During the stirring, 1N aqueous sodium hydroxide was added to adjust pH 8-9 continuously. After confirming termination of the reaction by TLC, the reaction mixture was diluted with aqueous ammonia (5 ml)-water (10 ml), and the mixture was extracted with chloroform. The organic layer was dehydrated by adding anhydrous sodium sulfate, filtered off sodium sulfate and distilled off the solvent to obtain crude product. The crude product was purified using thin layer chromatography with chloroform-methanol-aqueous ammonia (50:1:0.1) to yield EM852 (88.1 mg, 83%, white powder).

EM852: M.p.: 94-96° C.;
HRMS (FAB) m/z: calculated for $C_{48}H_{83}NO_{14}Na$ [M+]$^+$ 920.5711, found 920.5743.

EXAMPLE 13

Synthesis of 4",13-Di-O-hexanoyl-de(3'-N-methyl)-N-ethyl-8,9-Anhydro-pseudoerythromycin A 6,9-hemiketal (EM853)

Ethyl iodide (14.8 µL, 0.185 mmol) was added to chloroform (1.2 mL) solution of EM777 (33.2 mg, 0.037 mmol) and N,N-diisopropylamine (32.2 µL, 0.185 mmol), and stirred at 50° C. for 3 hours. After confirming termination of the reaction by TLC, the reaction mixture was diluted with water (10 ml) and extracted with chloroform. The organic layer was dehydrated by adding anhydrous sodium sulfate, and the sodium sulfate was filtered off, then the solvent was distilled off to obtain the crude product. After removed off methanol, the residue was purified by using thin layer chromatography with chloroform-methanol-aqueous ammonium (100:1:0.1) to yield EM853 (24.0 mg, 70%, white powder).

EM853: M.p.: 94-96° C.;
HRMS (FAB) m/z: calculated for $C_{50}H_{87}NO_{14}Na$ [M+Na]$^+$ 948.6024, found 948.6024.

EXAMPLE 14

Synthesis of 2'-O-acetyl-4"-O-benzenesulfonyl-12,13-epoxy-8,9-Anhydro-pseudoerythromycin A 6,9-hemiketal (EM774)

To EM718 (62.5 mg, 0.0825 mmol) dissolved in pyridine (1.7ml) was added drop wise benzene sulfonyl chloride (105.3 µL, 0.825 mmol) at room temperature, then DMAP (trace) was added to the solution. The reaction mixture was stirred at room temperature for 48 hours. The mixture was poured into water to terminate the reaction and extracted with dichloromethane. The extract was washed with saturated brine, dried over anhydrous sodium sulfate, filtered, and distilled off the solvent to obtain crude product. The crude product was purified by thin layer chromatography with chloroform-methanol-aqueous ammonia (15:1:0.1) to yield EM774 (42.0 mg, 58%, white powder).

EM774: M.p.: 94-96° C.;
IR (KBr) v: 2973.7, 2939.0, 2881.1, 2859.9, 2832.9, 2782.8, 1743.3, 1420.2, 1371.1, 1346.1, 1243.9, 1187.9, 1126.2, 1095.4, 1051.1, 1016.3 cm$^{-1}$;
HRMS (FAB) m/z: calculated for $C_{45}H_{70}NO_{14}S$ [M +H]$^+$ 880.45.17, found 880.4545.

EXAMPLE 15

Synthesis of 2'-O-acetyl-4"-O-benzylsulfonyl-12,13-epoxide-8,9-anhydro-pseudoerythromycin A. 6,9-hemiketal (EM775)

To EM718 (62.5 mg, 0.0825 mmol) dissolved in pyridine (1.7 ml) was added dropwise benzene sulfonyl chloride (157.3 µL, 0.825 mmol) at room temperature, then DMAP (trace) was added to the solution. The reaction mixture was stirred at room temperature for 48 hours. The mixture was poured into water to terminate the reaction and extracted with dichloromethane. The extract was washed with saturated brine, dried over anhydro sodium sulfate, filtered, and distilled off the solvent to obtain crude product. The crude product was purified by thin layer chromatography with chloroform-methanol-aqueous ammonia (15:1:0.1) to yield EM775 (57.2 mg, 78%, white powder).

EM775: M.p.: 103-106° C.;
IR (KBr) v: 2967.9, 2931.3, 2831.0, 1749.1, 1731.8, 1633.4, 1456.0, 1369.2, 1340.3, 1240.0, 1170.6, 1130.1, 1095.4, 1056.8, 1002.8, 966.2 cm$^{-1}$;
HRMA (FAB) m/z: calculated for $C_{46}H_{72}NO_{14}S$ [M+H]$^+$ 894.4674, found 894.4673.

EXAMPLE 16

Synthesis of 4"-O-benzylsulfonyl-12,13-epoxy-8,9-anhydro-pseudoerythromycin A. 6,9-hemiketal (EM780)

EM775 (11.5 mg, 0.0129 mmol) was dissolved in methanol (4.0 mL) and dichloromethane (2 mL), then stirred at room temperature for 48 hours. After removal of methanol in vacuo, the residue was purified by thin layer chromatography with chloroform-methanol-aqueous ammonia (15:1:0.1) to yield EM780 (10.1 mg, 92%, white powder).

EM780: M.p.: 197- 199° C.;
IR (KBr) v: 3463.5, 2971.8, 2939.0, 2886.9, 1735.6, 1457.9, 1384.6, 1340.3, 1247.7, 1172.5, 1093.4, 1051.0, 1016.3, 962.3, 916.0, 887.1 cm$^{-1}$;
HRMS (FAB) m/z: calculated for $C_{44}H_{70}NO_{13}S$ [M+H]$^+$ 852.4568, found 852.4567.

REFERENCE EXAMPLE 3

Synthesis of 9(E)-oxime erythromycin A [E9(E)-oxime]

Synthesis of 9-oxime erythromycin A was described in Richard S. Egan, Leslie A. Freiberig, and Wolliam H. Washbum, J. Org. Chem. 39 (17) 2492-2494 (1974).

Erythromycin A (15 g, 21 mmol) was dissolved in methanol (225 ml). Triethylamine (9.6 ml) and hydroxylamine hydrochloride (6.3 mg, 91 mmol) were added thereto and refluxed for 96 hours. The reaction mixture was cooled, diluted with water (2.6 lit.) and extracted with chloroform (2.6 lit.). Chloroform layer was dehydrated by adding anhydrous sodium sulfate, and distilled off the solvent to obtain the crude product. The crude product was purified with silica gel column chromatography using chloroform-methanol-aqueous ammonia (10:0.5:0.1) to yield the compound in the title (12.3 g, 84%, amorphous white solid).

EXAMPLE 17

Synthesis of 9(E)-4-morpholino-2-butenyloxime-erythro-mycin A (EM762)

EM(9)-oxime (96.2 mg, 0.129 mmol) was dissolved in DMF (1.3 mL) and ethyl ether (2.6 mL). Sodium hydride (60%)(7.1 mg, 0.193 mmol) and 1,4-bromo-2-butene (32.9 mg, 0.154 mmol) were added to the solution sequentially. After stirring for 1 hour at room temperature, piperazine (4.4 mg, 0.0514 mmol) and N,N-diisopropylethylamine (67.2 µL, 0.386 mmol) were added to the reaction mixture. The reaction mixture was stirred at room temperature for 12 hours, then poured into water to terminate the reaction and extracted with dichloromethane. The organic layer was washed with saturated brine, dried over anhydrous sodium sulfate, filtered, distilled off the solvent to obtain crude product. The crude product was purified by thin layer chromatography with chloroform-methanol-aqueous ammonia (20:1:0.1) to yield EM762 (38.9 mg, 34%, white powder).

EM762: M.p.: 124-126° C.;

IR (KBr) v: 3425.0, 2973.7, 2939.0, 2879.2, 2829.1, 1735.6, 1633.4, 1459.8, 1378.9, 1344.1, 1282.4, 1168.7, 1112.7, 1085.7, 1052.9, 1000.9 cm$^{-1}$;

HRMS (FAB) m/z: calculated for $C_{45}H_{82}N_4O_{13}Na$ [M+Na]$^+$ 909.5767, found 909.5774.

EXAMPLE 18

Synthesis of 9(E)-4-(amino ethylamino)-2-butenyloxime-erythromycin A (EM763)

EM9(E)-oxime (51.2 mg, 0.0684 mmol) was dissolved in DMF (0.6 mL) and ethyl ether (1.4 mL). Sodium hydride (60%) (4.2 mg, 0.103 mmol) and 1,4-bromo-2-butene (17.6 mg, 0.0820 mmol) were added to the solution sequentially. After stirring for 1 hour at room temperature, ethylenediamine (2.4 µL, 0.0342 mmol) and N,N-diisopropylethylamine (35.8 µL, 0.206 mmol) were added to the reaction mixture. The reaction mixture was stirred at room temperature for 16 hours, then poured into water to terminate the reaction and extracted with dichloromethane. The organic layer was washed with saturated brine, dried over anhydrous sodium sulfate, filtered, and distilled off the solvent to obtain crude product. The crude product was purified by thin layer chromatography with chloroform-methanol-aqueous ammonia (20:1:0.1) to yield EM763 (22.6 mg, 38%, white powder).

EM763: M.p.: 105-108° C.;

IR (KBr) v: 3446.2, 3430.7, 2973.7, 2939.0, 2877.3, 1735.6, 1625.7, 1457.9, 1378.9, 1346.1, 1284.4, 1168.7, 1110.8, 1085.7, 1052.9, 1012.4 cm$^{-1}$;

HRMS (FAB) m/z: calculated for $C_{43}H_{81}N_4O_{13}$ [M+H]$^+$ 861, found 861.

EXAMPLE 19

Synthesis of 9(E)-3-butenyloxime-erythromycin A (EM769)

EM9(E)-oxime (92.3 mg, 0.123 mmol) was dissolved in DMF (3.1 mL) and ethyl ether (6.1 mL). Sodium hydride (60%) (7.4 mg, 0.185 mmol) and 1,4-bromo-2-butene (31.7 mg, 0.148 mmol) were added to the solution sequentially. After stirring for 1 hour at room temperature, hydrazine (31.0 µL, 0.987 mmol) was added to the reaction mixture. The reaction mixture was stirred at room temperature for 18 hours, then poured into water to terminate the reaction and extracted with dichloromethane. The organic layer was washed with saturated brine, dried over anhydrous sodium sulfate, filtered, and distilled off the solvent to obtain crude product. The crude product was purified by thin layer chromatography with chloroform-methanol-aqueous ammonia (15:1:0.1) to yield EM769 (34.0 mg, 34%, white powder).

EM769: M.p.: 102-104° C.;

IR (KBr) v: 3453.9, 3430.7, 2973.7, 2939.0, 2877.3, 1737.5, 1641.1, 1457.9, 1380.8, 1344.1, 1282.4, 1168.7, 1112.7, 1081.9, 1052.9, 1000.9 cm$^{-1}$;

HRMS (FAB) m/z: calculated for $C_{41}H_{74}N_2O_{13}Na$ [M+Na]$^+$ 825.5089, found 825.5056.

EXAMPLE 20

Synthesis of 3'-de-N-methyl-3'-N-{2-amino-(3'-de-N-methyl-erythromycin A)}ethyl-erythromycin A (EM752)

To de-N-methyl erythromycin A (34.5 mg, 0.0479 mmol) dissolved in DMF (1.6 mL) were added dropwise N,N-diisopropylethylamine (166.9 µL, 0.958 mmol) and 1-bromo-2-chloroethane (79.8 µL, 0.958 mmol) at room temperature. The reaction mixture was stirred at room temperature for 120 hours. The solution was diluted with water and extracted with dichloromethane. The organic phase was washed with saturated brine and dried over anhydrous sodium sulfate. After the evaporation of the solvent, the residue was purified by thin layer chromatography with chloroform-methanol-aqueous ammonia (15:1:0.1) to yield EM752 (21.0 mg, 60%, white powder).

EM752: M.p.: 164-167° C.;

IR (KBr) v: 3455.8, 2971.6, 2937.1, 1729.8, 1693.2, 1457.9, 1378.9, 1344.1, 1284.4, 1168.7, 1108.9, 1079.9, 1054.9, 1012.4 cm$^{-1}$;

LRMS (FAB) m/z: calculated for $C_{74}H_{133}N_2O_{26}$ [M+H]$^+$ 1465, found 1465.

EXAMPLE 21

Synthesis of 3'-de-N-methyl-3'-N-{2-amino-(3'-de-N-metHyl-clarythromycin A)}ethyl-clarythromycin (EM753)

To de-N-methyl clarythromycin (93.2 mg, 0.127 mmol) dissolved in DMF (1.6 mL) were added dropwise N,N-diisopropylethylamine (442.4 µL, 2.540 mmol) and 1-bromo-2-chloroethane (211.4 µL, 2.540 mmol) at room temperature. The reaction mixture was stirred at room temperature for 120 hours. The solution was diluted with water and extracted with dichloromethane. The organic phase was washed with saturated brine and dried over anhydrous sodium sulfate. After evaporation of the solvent, the residue was purified by thin layer chromatography with chloroform-methanol-aqueous ammonia (20:1:0.1) to yield EM753 (74.2 mg, 78%, white powder).

EM753: M.p.: 188-191° C.;

IR (KBr) v: 3461.6, 2971.8, 2937.1, 1733.7, 1691.3, 1629.6, 1459.8, 1405.9, 1378.9, 1346.1, 1286.3, 1245.8, 1168.7, 1110.8, 1083.8, 1054.9 cm$^{-1}$;

LRMS (FAB) m/z: calculated for $C_{76}H_{137}N_2O_{26}$ [M+H]$^+$ 1493, found 1493.

EXAMPLE 22

Synthesis of 3'-de-N-methyl-3'-N-{4-amino-(3'-de-N-methyl-erythromycin A)}-2(E)-butenyl-erythromycin A (EM757)

1,4-bromo-2-butene (8.4 mg, 0.0393 mmol) and N,N-diisopropylethylamine (41.0 µL, 0.236 mmol) were added to the solution of de-N-methyl erythromycin A (56.5 mg, 0.0785 mmol) dissolved in dichloromethane (2.6 mL) at room temperature. The reaction mixture was stirred at room temperature for 120 hours. The mixture was poured into water to terminate the reaction and extracted with dichloromethane. The extract was washed with saturated brine, dried over anhydrous sodium sulfate, filtered, and distilled off the solvent to obtain the crude product. The crude product was purified by thin layer chromatography with chloroform-methanol-aqueous ammonia (20:1:0.1) to yield EM757 (35.1 mg, 60%, white powder).

EM757: M.p.: 151-154° C.;
IR (KBr) v: 3519.5, 3473.2, 2973.7, 2940.9, 2879.2, 1714.4, 1637.3, 1459.8, 1376.9, 1348.0, 1284.4, 1270.9, 1240.0, 1193.7, 1170.6, 1108.9, 1085.7, 1052.9, 1008.6 cm$^{-1}$;
LRMS (FAB) m/z: calculated for $C_{76}H_{135}N_2O_{26}$ [M+H]$^+$ 1491, found 1491.

EXAMPLE 23

Synthesis of 3'-de-N-methyl-3'-N-{4-amino-(3'-de-N-methyl-clarythromycin A)}-2(E)-butenyl-clarythromycin A (EM758)

1,4-bromo-2-butene (5.8 mg, 0.0271 mmol) was added to the solution of de-N-methyl-clarythromycin (39.8 mg, 0.0542 mmol) and N,N-diisopropylethylamine (28.3 µL, 0.163 mmol) in dichloromethane (1.8 mL) at room temperature. The reaction mixture was stirred at room temperature for 120 hours. The mixture was poured into water and extracted with dichloromethane. The extract was washed with satyrated brine, dried over anhydrous sodium sulfate, filtered, and distilled off the solvent to obtain crude product. The crude product was purified by thin layer chromatography with chloroform-methanol-aqueous ammonia (20:1:0.1) to yield EM758 (26.3 mg, 66%, white powder).

EM758: M.p.: 167-169° C.;
IR (KBr) v: 3619.7, 3453.9, 3426.9, 2973.7, 2939.0, 1735.6, 1689.3, 1457.9, 1407.8, 1378.9, 1346.1, 1286.3, 1170.6, 1110.8, 1083.8, 1052.9, 1010.5 cm$^{-1}$;
LRMS (FAB) m/z: calculated for $C_{78}H_{139}N_2O_{26}$ [M+H]$^+$ 1519, found 1519.

EXAMPLE 24

Synthesis of 9(E)-4-{9(E)-oxime-erythromycin A}-2-butenyloxime-erythromycin A (759)

EM9(E)-oxime (99.8 mg, 0.133 mmol) was dissolved in DMF (1.33 mL) and ethyl ether (1.33 ml). Sodium hydride (60%) (8.0 mg, 0.200 mmol) and 1,4-bromo-2-butene (14.3 mg, 0.0667 mmol) were added to the solution sequentially. After stirring for 1 hour at room temperature, the reaction mixture was poured into water to terminate the reaction and extracted with dichloromethane. The organic layer was washed with saturated brine, dried over anhydrous sodium sulfate, filtrated, and distilled off the solvent to obtain the crude product. The crude product was purified by thin layer chromatography with chloroform-methanol-aqueous ammonium (20:1:0.1) to yield EM759 (64.0 mg, 62%, white powder).

EM759: M.p.: 138-140° C.;
IR (KBr) v: 3448.1, 3423.0, 2973.7, 2939.0, 1735.6, 1623.8, 1457.9, 1405.9, 1380.8, 1344.1, 1280.5, 1168.7, 1112.7, 1085.7, 1052.9, 1000.9 cm$^{-1}$;
LRMS (FAB) m/z: calculated for $C_{78}H_{141}N_4O_{28}$ [M+H]$^+$ 1549, found 1549.

EXAMPLE 25

Synthesis of 9(E)-4-piperazine-{N-4-(9(E)-oxime-erythro mycin A-2(E) butenyl}-2-butenyloxime-erythromycin A (EM760)

EM9(E)-oxime (96.2 mg, 0.129 mmol) was dissolved in DMF (1.3 mL) and ethyl ether (2.6 mL). Sodium hydride (60%) (7.1 mg, 0.193 mmol) and 1,4-bromo-2-butene (32.9 mg, 0.154 mmol) were added to the solution sequentially. After stirring for 1 hour at room temperature, piperazine (4.4 mg, 0.0514 mmol) and N,N-diisopropylethylamine (67.2 µL, 0.386 mmol) were added to the reaction mixture. The reaction mixture was further stirred at room temperature for 12 hours, then poured into water to terminate the reaction and extracted with dichloromethane. The organic layer was washed with saturated brine, dried over anhydrous sodium sulfate, filtered, and distilled off the solvent to obtain the crude product. The product was purified by thin layer chromatography with chloroform-methanol-aqueous ammonia (20:1:0.1) to yield EM760 (41.7 mg, 38%, white powder).

EM760: M.p.: 152-155° C.;
IR (KBr) v: 3452.0, 3423.0, 2973.7, 2937.1, 2879.2, 1733.7, 1633.4, 1456.0, 1378.9, 1346.1, 1282.4, 1168.7, 1110.8, 1085.7, 1052.9, 1002.8 cm$^{-1}$;
LRMS (FAB) m/z: calculated for $C_{86}H_{156}N_6O_{26}$ [M+H]$^+$ 1688, found 1688.

EXAMPLE 26

Synthesis of 9(E)-4-amino-{N-$^4$-(9(E)-oxime-erythromycin A)-2-butenyl}-2-butenyloxime-erythromycin A (EM761)

EM9(E)-oxime (51.2 mg, 0.0684 mmol) was dissolved in DMF (0.6 mL) and ethyl ether (1.4 mL). Sodium hydride (60%) (4.2 mg, 0.103 mmol) and 1,4-bromo-2-butene (17.6 mg, 0.0820 mmol) were added to the solution sequentially. After stirring for 1 hour at room temperature, ethylenediamine (2.4 µL, 0.0342 mmol) and N,N-diisopropylethylamine (35.8 µL, 0.206 mmol) were added to the reaction mixture. The reaction mixture was stirred at room temperature for 16 hours, then poured into water to terminate the reaction and extracted with dichloromethane. The organic layer was washed with saturated brine, dried over anhydrous sodium sulfate, filtered, and distilled off the solvent to obtain the crude product. The crude product was purified by thin layer chromatography with chloroform-methanol-aqueous ammonia (20:1:0.1) to yield EM761 (14.2 mg, 25%, white powder).

EM761: M.p.: 140-143° C.;
IR (KBr) v: 3467.4, 3428.8, 3423.0, 2973.7, 2939.0, 2877.3, 1733.7, 1627.6, 1459.8, 1378.9, 1348.0, 1282.4, 1168.7, 1112.7, 1085.7, 1052.9, 1012.4 cm$^{-1}$;
LRMS (FAB) m/z: calculated for $C_{84}H_{152}N_6O_{26}Na$ [M+H]$^+$ 1684, found 1684.

EXAMPLE 27

Synthesis of 9(E)-4-{9(E)-oxime-erythromycin A}-2 (E)buthyloxime-erythromycin A (EM764)

To the mixture palladium on activated carbon (4.0 mg) in ethanol (2.6 mL) was added EM759 (19.9 mg, 0.0129 mmol). The reaction mixture was stirred under H$_2$ (1 atm) at room temperature for 48 hours. The mixture was filtered with celite and washed with ethanol. After distilled off the solvent, the residue was purified by thin layer chromatography with chloroform-methanol-aqueous ammonia (15:1:0.1) to yield EM764 (16.5 mg, 83%, white powder).

EM764: M.p.: 150-153° C.;
IR (KBr) v: 3455.8, 3436.5, 2973.7, 2939.0, 2877.3, 1737.5, 1627.6, 1459.8, 1380.8, 1344.1, 1280.5, 1168.7, 1085.7, 1052.9, 1012.4 cm$^{-1}$;

LRMS (FAB) m/z: calculated for $C_{78}H_{143}N_4O_{26}$ [M+H]$^+$ 1551, found 1551.

REFERENCE EXAMPLE 4

Synthesis of 3'-de-N-methyl erythromycin A (EM798)

Synthesis of EM798 is described in L. A. Freiberg and Japanese Patent Kokai Hei 47-9129A. Sodium acetate (146.4 mg, 1.785 mmol) and iodine (99.6 mg, 0.392 mmol) were added sequentially to the stirred solution of erythromycin A (267.0. mg, 0.375 mmol) in methanol (58.0 mL) and water (12.0 mL) at room temperature. The reaction mixture was stirred at 50° C. for 3.5 hours. During the reaction, 1N aqueous solution of sodium hydroxide was added dropwise to adjust the pH of the solution to 8.0-9.0. The reaction mixture was concentrated in vacuo to remove the methanol. The residue was dissolved in saturated brine and extracted with dichloromethane. The extracts were dried over anhydrous sodium sulfate, and distilled off the solvent to obtain the crude product. The resulting crude product was purified by column chromatography on silica gel eluting with chloroform-methanol-aqueous ammonia (10:0.5:0.1) to give EM798 (221.0 mg, 84%, white amorphous solid).

EXAMPLE 28

Synthesis of 3'-de-N-methyl-3'-N-{4-9(E)oxime-erythro-mycin A}-2(E)-butenyl-erythromycin A (EM765)

EM9(E)-oxime (68.6 mg, 0.0967 mmol) was dissolved in DMF (1.0 mL) and ethyl ether (1.9 mL). Sodium hydride (60%) (5.5 mg, 0.137 mmol) and 1,4-bromo-2-buten (23.5 mg, 0.110 mmol) were added to the solution sequentially. After stirring for 1 hour at room temperature, EM798 (66.0 mg, 0.0967 mmol) and N,N-diisopropylamine (47.9 µL, 0.275 mmol) were added to the reaction mixture. The reaction mixture was stirred at room temperature for 18 hours, then poured into water to terminate the reaction and extracted with dichloromethane. The organic layer was washed with saturated brine, dried over anhydrous sodium sulfate, filtered, and distilled off the solvent to obtain the crude product. The crude product was purified by thin layer chromatography with chroloform-methanol-aqueous ammonia (20:1:0.1) to yield EM765 (37.6 mg, 25%, white powder).

EM765: M.p.: 148-151° C.;

IR (KBr) ν: 3448.1, 3436.5, 2973.7, 2939.0, 2879.2, 1733.7, 1635.3, 1459.8, 1378.9, 1346.1, 1284.4, 1168.7, 1110.8, 1085.7, 1052.9, 1012.4 cm$^{-1}$;

LRMS (FAB) m/z: calculated for $C_{77}H_{138}N_3O_{26}$ [M+H]$^+$ 1520, found 1520.

EXAMPLE 29

Synthesis of 3'-de-N-methyl-3'-N-{-amino-(3'-de-N-methyl-anhydro-pseudoerythromycin A 6,9-hemiketal)}ethyl-anhydro-pseudoerythromycin A 6,9-hemiketal (EM741)

To EM703 (72.4 mg., 0.103 mmol) dissolved in DMF (3.4 mL) was added dropwise N,N-diisopropylethylamine (359.5 µL, 2.064 mmol) and 1-bromo-2-chloroethane (171.8 µL, 2.064 mmol) at room temperature. The reaction mixture was stirred at room temperature for 48 hours. The solution was diluted with water and extracted with dichloromethane. The organic layer was washed with saturated brine and dried over anhydrous sodium sulfate. After distilled off the solvent, the residue was purified by thin layer chromatography with chloroform-methanol-aqueous ammonia (15:1:0.1) to yield EM741 (38.7 mg, 53%, white powder). 10.2 mg of EM703 was recovered (14%)

EM741: M.p.: 149-152° C.;

IR (KBr) ν: 3675.7, 2971.8, 2935.1, 2879.2, 1708.6, 1631.5, 1457.9, 1378.9, 1263.1, 1166.7, 1112.7, 1074.2, 1049.1, 1039.4, 1016.3 cm$^{-1}$;

LRMS (FAB) m/z: calculated $C_{74}H_{129}N_2O_{24}$ [M+H]$^+$ 1429, found 1429.

Biologically Properties

Enhancing action for activities of azole antifungal agents is explained in detail hereinbelow.

Test organisms used were *Candida albicans* ATCC 64548, fluconazole resistant *Candida albicans* ATCC 64550 and *Aspergillus niger* ATCC 6275. *Candida* spp. were cultured in Waksman broth (glucose 2.0%, peptone 0.5%, dry yeast 0.3%, meat extract 0.5%, NaCl 0.5% and $CaCO_3$ 0.3%, pH 7.0) at 27° C. for 40 hours, then 0.1% thereof was inoculated on GY agar medium (glucose 1.0%, yeast extract 0.5% and agar 0.8%, pH 6.0). Spore suspension 0.2% of *Aspergillus niger* ATCC 6275 was inoculated on GY agar medium.

Azole antifungal agents used were miconazole (Sigma Inc., the U.S.) and fluconazole (ICN Pharmaceuticals, Inc., the U.S.), and were added at concentrations without affecting growth on each test organisms follows.

*Candida albicans* ATCC 64548: miconazole 0.03 µg/ml or fluconazole 0.5 µg/ml.

*Candida albicans* ATCC 64550: miconazole 0.15 µg/ml or fluconazole 30 µg/ml.

*Aspergillus niger* ATCC 6275: miconazole 0.1 µg/ml or fluconazole 10 µg/ml.

In the above medium, a medium added with miconazole to GY medium (control) is designated as GYM, and a medium added with fluconazole is designated as GYF. Activities were assessed by means of paper disk method (thickness: 8 mm, ADVANTEC MFS INC., Japan). Diameter of inhibition ring is expressed with mm unit after culturing *Candida* spp. for 24 hours and *Aspergillus niger* ATCC 6275 for 48 hours. Transparency of the inhibition ring is assessed with 5 degrees of A, B, C, D and E (transparence<A<B<C<D<E<opaque). Each transparency indicates in the following and results are showed in Table 1.

A: Growth of test organism was inhibited 95% or more.

B: Growth of test organism was inhibited 75% of more and 95% or less.

C: Growth of test organism was inhibited 55% or more and 75% or less.

D: Growth of test organism was inhibited 35% or more and 55% or less.

E: Growth of test organism was inhibited 35% or less.

N.T.: Not test.

TABLE 1

| Compound Sample No | (μg/8 mm disk) | Inhibition activity (inhibition ring mm) | | | | | | | | |
|---|---|---|---|---|---|---|---|---|---|---|
| | | C. albicans ATCC 64548 | | | C. albicans ATCC 64550 | | | A. niger ATCC 6275 | | |
| | | GY | GYM | GYF | GY | GYM | GYF | GY | GYM | GYF |
| 719 | 10 | — | 9E | — | — | — | — | — | — | — |
| | 50 | — | 10E | — | — | — | — | — | — | — |
| | 100 | — | 13E | — | — | — | — | — | — | — |
| 755 | 10 | — | — | — | — | — | — | — | — | — |
| | 50 | — | — | — | — | — | — | — | 16E | — |
| | 100 | — | 17D | — | — | 10E | — | — | N.T. | — |
| 756 | 10 | — | — | — | — | — | — | — | — | — |
| | 50 | — | — | — | — | — | — | 10E | 14E | 14E |
| | 100 | — | 15D | — | — | 10E | — | N.T. | N.T. | N.T. |
| 770 | 10 | — | 11D | — | — | — | — | — | — | 11E |
| | 50 | — | 14C | — | — | 13A | 13C | 11E | 12E | 18E |
| | 100 | — | N.T. | 11D | N.T. | N.T. | N.T. | N.T. | N.T. | N.T. |
| 771 | 10 | — | — | — | — | — | — | — | — | 14E |
| | 50 | — | 12D | — | — | 10A | 10E | — | 23E | 15E |
| | 100 | N.T. | N.T. | N.T. | N.T. | N.T. | N.T. | N.T. | N.T. | N.T. |
| 772 | 10 | — | 14B | 9D | — | — | 11E | — | 12E | 10D |
| | 50 | — | 12B | 10D | — | 12A | 14B | 12E | 13A | 10D |
| | 100 | N.T. | N.T. | N.T. | N.T. | N.T. | N.T. | N.T. | N.T. | N.T. |
| 773 | 10 | — | 13C | — | — | 10C | 11E | — | 13E | 10E |
| | 50 | — | 16A | 12E | — | 14A | 15A | — | 15B | 15E |
| | 100 | N.T. | N.T. | N.T. | N.T. | N.T. | N.T. | N.T. | N.T. | N.T. |
| 776 | 10 | — | — | — | — | — | — | — | — | 16E |
| | 50 | — | 11D | — | — | 11E | 9E | — | 20C | 16E |
| | 100 | — | N.T. | 15E | N.T. | N.T. | N.T. | N.T. | N.T. | N.T. |
| 777 | 10 | — | 11D | — | — | — | 11D | — | 11E | 11E |
| | 50 | — | 14A | 11D | — | 14A | 14A | 9E | 13B | 17D |
| | 100 | N.T. | N.T. | N.T. | N.T. | N.T. | N.T. | N.T. | N.T. | N.T. |
| 778 | 10 | — | 12B | — | — | — | 10E | — | 14E | 12E |
| | 50 | — | 16A | 9D | — | 14B | 13B | 10E | 16A | 13D |
| | 100 | N.T. | N.T. | N.T. | N.T. | N.T. | N.T. | N.T. | N.T. | N.T. |
| 779 | 10 | — | 10E | — | — | — | — | — | — | 11E |
| | 50 | — | 15A | 9D | — | 11D | 10E | 11E | 17E | 13D |
| | 100 | N.T. | N.T. | N.T. | N.T. | N.T. | N.T. | N.T. | N.T. | N.T. |
| 852 | 10 | — | — | — | — | 9C | 9C | — | — | — |
| | 50 | — | 9A | — | — | 10B | 11A | 9E | 8C | 8D |
| | 100 | — | 10A | — | — | 12B | 12A | 10E | 9A | 9D |
| 853 | 10 | — | 10B | 9E | — | — | 11D | 10E | 10E | 9E |
| | 50 | — | 14A | 14B | — | 15A | 14A | 12D | 15B | 13B |
| | 100 | — | 15A | 16B | — | 16A | 15A | 13D | 16B | 14B |
| 774 | 10 | — | — | — | — | 14A | 13A | — | 13E | 14E |
| | 50 | — | — | — | — | 17A | 17A | — | 18D | 17E |
| | 100 | N.T. | N.T. | N.T. | N.T. | N.T. | N.T. | N.T. | N.T. | N.T. |
| 775 | 10 | — | — | — | — | — | — | — | — | 16E |
| | 50 | — | 10E | — | — | — | — | — | 16D | 16E |
| | 100 | N.T. | N.T. | N.T. | — | — | — | N.T. | N.T. | N.T. |
| 780 | 10 | — | — | — | — | — | — | — | 14E | 11E |
| | 50 | — | — | — | — | 12C | 14C | 12E | 14E | 12E |
| | 100 | N.T. | N.T. | N.T. | N.T. | N.T. | N.T. | N.T. | N.T. | N.T. |
| 762 | 10 | — | — | — | — | — | — | — | — | 14E |
| | 50 | — | 13D | — | — | — | — | — | — | 15E |
| | 100 | — | N.T. | — | — | — | — | — | — | N.T. |
| 763 | 10 | — | — | — | — | — | — | — | — | 12E |
| | 50 | — | 16C | 10D | — | — | — | — | — | 15E |
| | 100 | N.T. | N.T. | N.T. | — | — | — | — | — | N.T. |
| 769 | 10 | — | — | — | — | — | — | — | — | 11E |
| | 50 | — | — | — | — | — | — | 10E | — | 16E |
| | 100 | — | 14E | — | — | — | — | N.T. | — | N.T. |
| 752 | 10 | — | — | — | — | — | — | — | — | — |
| | 50 | — | — | — | — | — | — | — | — | 17E |
| | 100 | — | 12E | — | — | — | — | — | — | N.T. |
| 753 | 10 | — | 17C | — | — | — | — | — | — | — |
| | 50 | — | 22C | — | — | — | — | — | — | — |
| | 100 | — | N.T. | — | — | — | — | — | 13E | — |
| 757 | 10 | — | — | — | — | — | — | — | — | — |
| | 50 | — | — | — | — | — | — | 10E | — | — |
| | 100 | — | 18D | 17E | — | — | — | — | — | — |
| 758 | 10 | — | 11E | — | — | — | — | — | — | — |
| | 50 | — | 12D | — | — | — | — | — | — | — |
| | 100 | — | N.T. | 15E | — | — | — | — | — | — |
| 759 | 10 | — | — | — | — | — | — | — | — | — |
| | 50 | — | — | — | — | — | — | — | — | — |
| | 100 | — | 13D | — | — | — | — | — | — | (—) |

TABLE 1-continued

| | | Inhibition activity (inhibition ring mm) | | | | | | | | |
|---|---|---|---|---|---|---|---|---|---|---|
| | | C. albicans ATCC 64548 | | | C. albicans ATCC 64550 | | | A. niger ATCC 6275 | | |
| Compound Sample No | (μg/8 mm disk) | GY | GYM | GYF | GY | GYM | GYF | GY | GYM | GYF |
| 760 | 10 | — | 10E | — | — | — | — | — | — | 15E |
| | 50 | — | 14D | — | — | — | — | — | — | 16E |
| | 100 | — | N.T. | — | — | — | — | — | — | N.T. |
| 761 | 10 | — | — | — | — | — | — | — | — | — |
| | 50 | — | — | — | — | — | — | — | — | — |
| | 100 | — | 14E | — | — | — | — | — | — | — |
| 764 | 10 | — | — | — | — | — | — | — | — | — |
| | 50 | — | 9E | — | — | — | — | — | — | — |
| | 100 | — | N.T. | — | — | — | — | — | — | — |
| 765 | 10 | — | — | — | — | — | — | — | — | 14E |
| | 50 | — | 14E | — | — | — | — | — | — | 21E |
| | 100 | — | N.T. | — | — | — | — | — | 14E | N.T. |
| 741 | 10 | — | — | — | — | — | — | — | — | — |
| | 50 | — | — | — | — | — | — | — | — | — |
| | 100 | — | 14D | — | — | — | — | — | — | — |

INDUSTRIAL APPLICABILITY

As explained hereinabove, since substances of the present invention have an action to enhance activities of azole antifungal agents against *Candida albicans* and *Aspergillus niger*, both of which include resistant strains, they have actions at low concentration and within short term against fungal infection and are useful for reducing frequency of appearance of resistant microorganisms. Further, combined use of two types of drugs having different skeletal structures or combined use of such drugs for resistant strains against azole compounds are expected to overcome resistance against azole antifungal agents.

What is claimed is:

1. A purified macrolide derivative, having an enhancing effect for activities of antifungal agents, represented by the formula [I]:

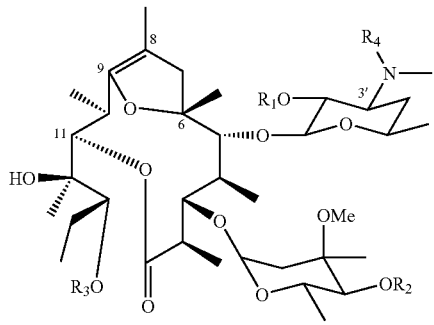

[I]

wherein when R1 is Ac, R2 and R3 are Ac, and R4 is Me; when R1 is H, R2 and R3 are Ac, and R4 is Me; when R1 is H, R2 and R3 are Ac, and R4 is H; when R1 is Bzl, R2 and R3 are Bzl, and R4 is Me; when R1 is Ac, R2 and R3 are Pr, and R4 is Me; when R1 is Ac, R2 and R3 are Hex, and R4 is Me; when R1 is Ac, R2 and R3 are Bzl, and R4 is Me; when R1 is H, R2 and R3 are Pr, and R4 is Me; when R1 is H, R2 and R3 are Hex, and R4 is Me; when R1 is H, R2 and R3 are Bzl, and R4 is Me; when R1 is H, R2 is H and R3 are Bzl, and R4 is Me; when R1 is H, R2 and R3 are Hex, and R4 is H; or when R1 is H, R2 and R3 are Hex, and R4 is Et.

2. A purified macrolide derivatives, having enhancing effect for activities of antifungal agents, represented by the formula [II]:

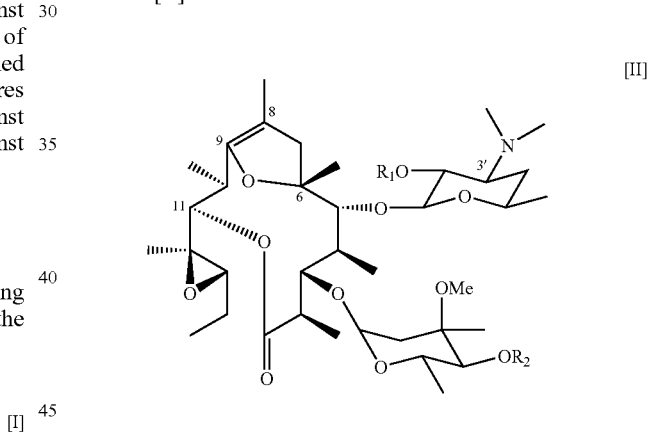

[II]

wherein when R1 is Ac, R2 is SO2Ph; when R1 is Ac, R2 is SO2Bn, or when R1 is H, R2 is SO2Bn.

3. A purified macrolide derivatives, having an enhancing effect for activities of antifungal agents, represented by the formula [III]:

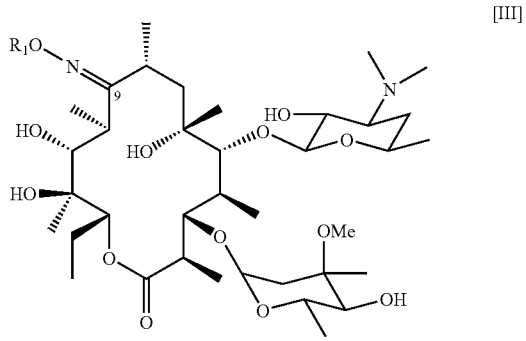

[III]

wherein R₁ is —CH₂CH=CHCH₂—N‾‾NH,

—CH₂CH=CHCH₂—NH‾‾NH₂ or —CH₂CH₂CH=CH₂.

4. A purified macrolide derivatives, having enhancing effect for activities of antifungal agents, represented by the formula [IV]:

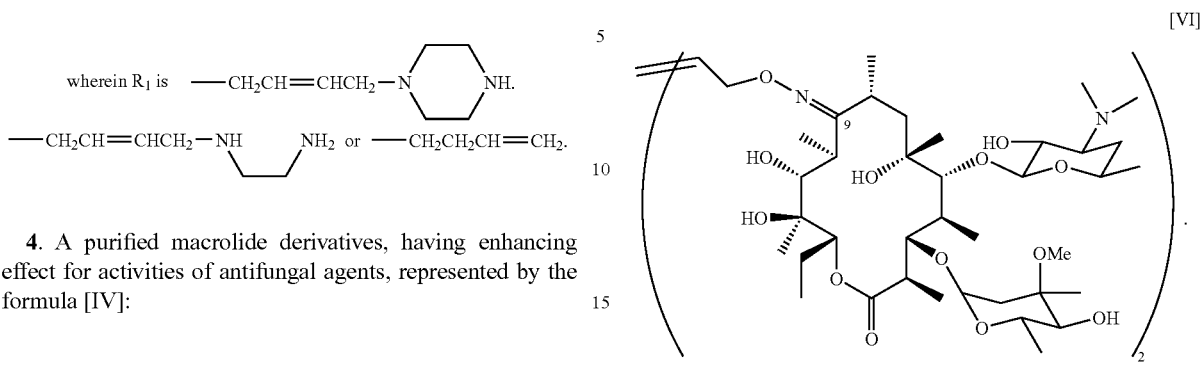

wherein R1 is H or Me.

5. A purified macrolide derivatives, having enhancing effect for activities of antifungal agents, represented by the formula [V]:

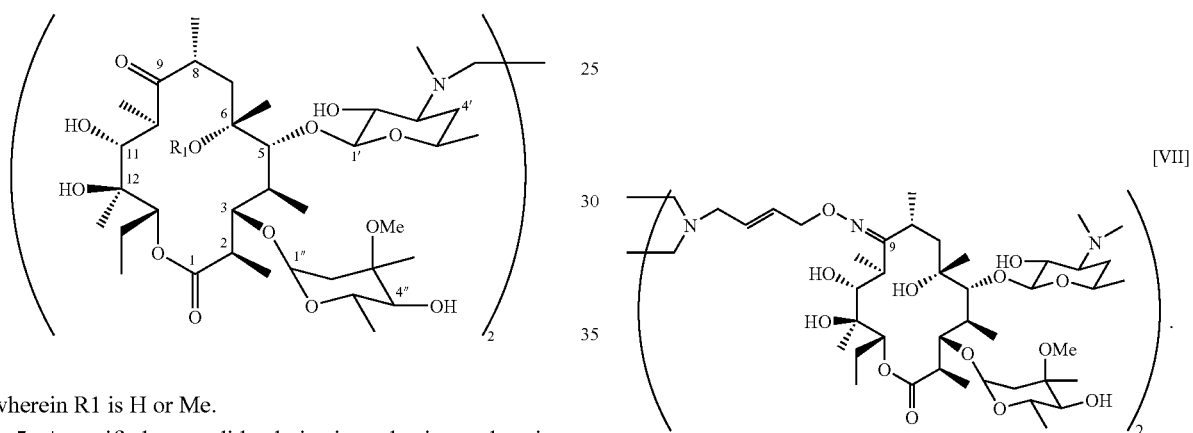

wherein R1 is H or Me.

6. A purified macrolide derivative, having enhancing effect for activities of antifungal agents represented by the formula [VI]:

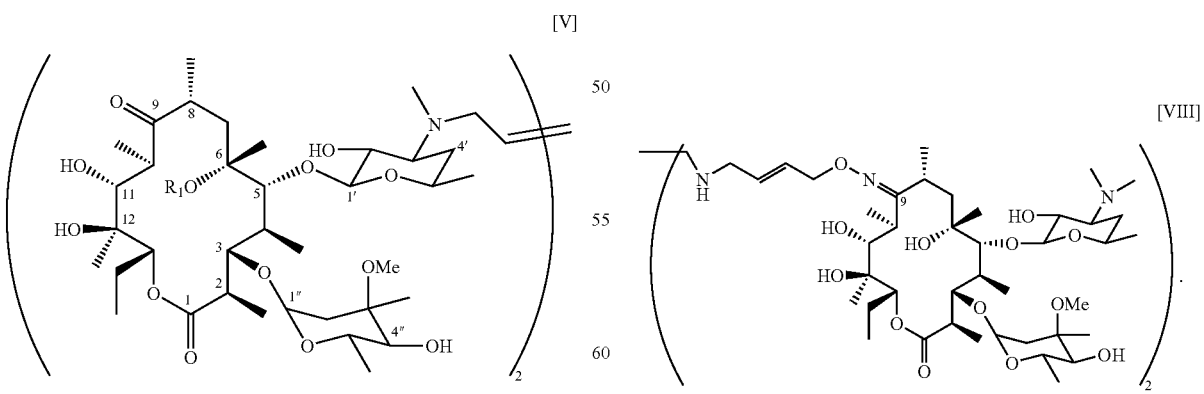

7. A purified macrolide derivative, having enhancing effect for activities of antifungal agents, represented by the formula [VII]:

8. A purified macrolide derivative, having enhancing effect for activities of antifungal agents, represented by the formula [VIII]:

9. A purified macrolide derivative, having enhancing effect for activities of antifungal agents, represented by the formula [IX]:

10. A purified macrolide derivative, having enhancing effect for activities antifungal agent, represented by the formula [IX]:

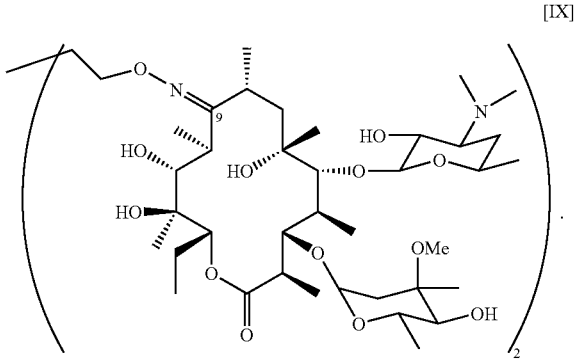

11. A purified macrolide derivative, having enhancing effect for activities of antifungal agents, represented by the formula [XI]:

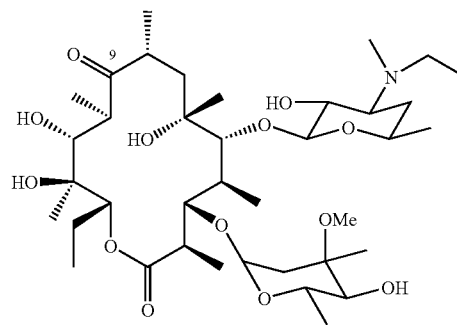

wherein $R_1$ is H.

12. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 1.

13. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 2.

14. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 3.

15. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 4.

16. A method for enhancing the activities of antifungal agents for the treatment of fungal infections accompanied by

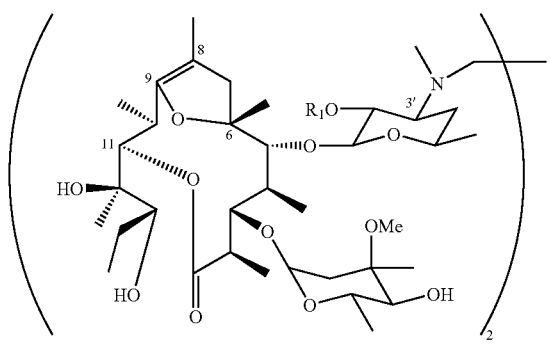

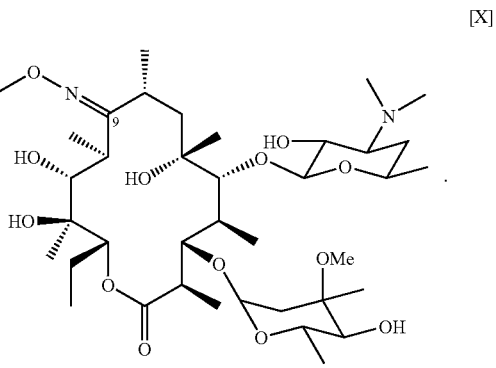

immunocommpromised conditions caused by HIV infection or blood diseases, comprising administering to a person in need thereof effective amounts of said antifungal agent and the macrolide derivative according to claim 5.

17. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 6.

18. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 7.

19. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 8.

20. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 9.

21. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 10.

22. A method for enhancing the activities of antifungal agents for the treatment of fungal infections accompanied by immunocommpromised conditions caused by HIV infection or blood diseases, comprising administering to a person in need thereof effective amounts of said antifungal agent and the macrolide derivative according to claim 11.

* * * * *